United States Patent
Rogers et al.

(10) Patent No.: US 6,663,670 B2
(45) Date of Patent: Dec. 16, 2003

(54) ADJUSTABLE LONG BONE PROSTHESIS

(75) Inventors: James R. Rogers, Winona Lake, IN (US); Joel C. Rhoades, Pierceton, IN (US); Troy D. Martin, Pierceton, IN (US)

(73) Assignee: DePuy Orthopaedics, Inc., Warsaw, IN (US)

( * ) Notice: Subject to any disclaimer, the term of this patent is extended or adjusted under 35 U.S.C. 154(b) by 150 days.

(21) Appl. No.: 10/051,341

(22) Filed: Jan. 18, 2002

(65) Prior Publication Data
US 2003/0139818 A1 Jul. 24, 2003

(51) Int. Cl.[7] ............................. A61F 2/28; A61F 2/30
(52) U.S. Cl. ............................. 623/23.47; 623/23.45
(58) Field of Search ............................. 623/16, 18, 20, 623/22, 23, 38, 23.45, 23.47

(56) References Cited

U.S. PATENT DOCUMENTS

| | | |
|---|---|---|
| 4,384,373 A | 5/1983 | Sivash |
| 4,502,160 A | 3/1985 | Moore et al. |
| 4,892,546 A | 1/1990 | Kotz et al. |
| 5,314,479 A | 5/1994 | Rockwood, Jr. et al. |
| 5,358,524 A | * 10/1994 | Richelsoph ............ 623/23.47 |
| 5,387,239 A | * 2/1995 | Bianco et al. ............ 623/23.45 |
| 5,876,459 A | 3/1999 | Powell |
| 5,906,644 A | 5/1999 | Powell |
| 6,290,725 B1 | 9/2001 | Weiss et al. |

* cited by examiner

Primary Examiner—Cary E. O'Connor
Assistant Examiner—Candice C. Melson
(74) Attorney, Agent, or Firm—Maginot, Moore & Beck

(57) ABSTRACT

A long bone prosthesis includes upper and lower articulating components, with the free ends of the components configured to engage a corresponding prosthetic joint. The overall length of the articulating components is adjustable to approximate the length of a patient's long bone, such as the humerus. The articulating components include a stem and collet arrangement for fixing the relative axial and rotational position of the components. A tapered lock nut is threaded onto the outer threaded surface of the collet portion to provide a pressure engagement of the articulating elements. Various surface features can be implemented among the components of the prosthesis to enhance the pressure fixation, restrict rotation or provide indexed movement of the articulating components relative to each other.

26 Claims, 3 Drawing Sheets

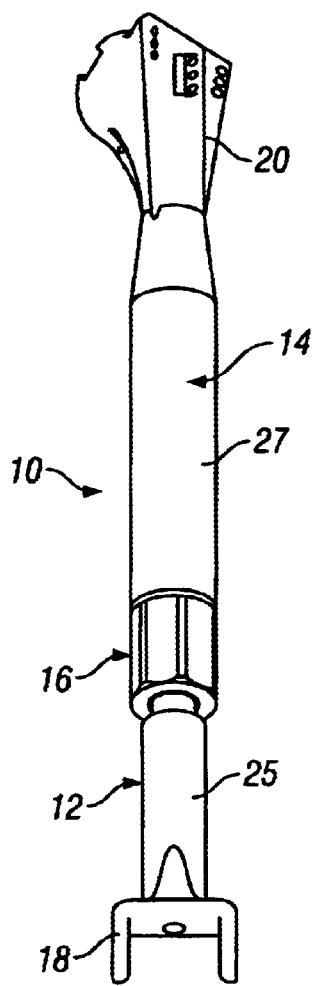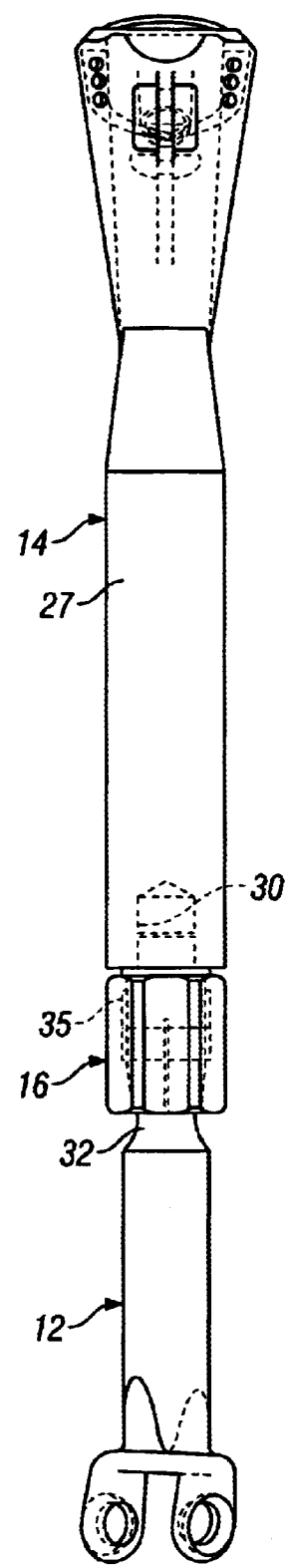
FIG. 1   FIG. 2

ADJUSTABLE LONG BONE PROSTHESIS

BACKGROUND OF INVENTION

The present invention relates to an orthopedic prosthesis. More specifically, the invention concerns a prosthesis for restoring the functionality of an extremity, such as an arm of a patient. The invention is particularly suited for the replacement of a long bone of the patient.

The later half of the 20$^{th}$ century has seen a proliferation in the number of human skeletal components that can be replaced by a man-made prosthesis. Over the years these prosthesis have evolved from simply a physical substitution for a bone or a joint, to the more sophisticated fully functional prosthesis. For example, prostheses are well known for the replacement of the shoulder joint or the elbow joint. A modular shoulder prosthesis designed according to U.S. Pat. No. 5,314,479, assigned to DePuy, Inc., can be integrated into the existing glenoid cavity of a patient's shoulder. The prosthesis includes a lower stem that is configured to be embedded within the existing humerus bone of the patient. In a like manner, U.S. Pat. No. 6,290,725 (also owned by Depuy, Inc.) discloses a modular elbow prosthesis that includes stems for implantation into the intramedullary canal of the humerus and ulna bones. Similar prosthetic joints exist for replacement of the hip, knee, and ankle joints.

While many devices exists for the replacement of a damaged or defective joint, the substitution of a bone, and particularly a long bone, is much more problematic. While prosthetic phalanges have enjoyed increasing success, the long bones have not been so easily replaced by a prosthesis, particularly to maintain the functionality of the patient's limb.

The problems with long bone replacement are many and varied. Perhaps the greatest difficulty is the extreme load-bearing nature of the long bones. One approach to this problem has been to supplement, rather than replace, the bone its self. For instance, as shown in U.S. Pat. No. 4,384,373, an artificial femoral diaphysis is extended through a longitudinal bore in the femur. The artificial diaphysis is bounded at one end by an artificial knee component and at its opposite end by an artificial hip component. This prosthesis of the '373 patent retains the existing bone and relies upon that bone for a certain amount of load-bearing capability.

A further problem associated with a long bone prosthesis is the variability in length of a particular long bone between patients. The femur, tibia, radius, and humerus bones vary in length as much as patients vary in height. The aforementioned '373 patent dealt with this variation by providing a motion screw and an external threaded sleeve feature for adjusting the overall distance between the hip joint and knee joint components of the prosthesis. Many similar approaches have been implemented for prosthetic joints. It should be noted that with these prostheses, the joint is affixed to an existing long bone, such as by implantation of a stem into the intramedullary canal of the bone. The following patents illustrate a variety of adjustable length features: U.S. Pat. Nos. 4,502,160; 4,892,546; 5,358,524; 5,387,239; and 5,906,644. These adjustable length features range from the bevel gear and external key arrangement of the '160 patent, to the Morse taper pressure lock feature of the device in the '644 patent.

One problem common to all of these prior adjustable length features is that the length of the prosthesis cannot be adjusted in situ. In other words, in each of the prior devices, the required length of the prosthesis is predetermined and the prosthesis adjusted before implantation into the patient. In a typical surgical procedure, the affected limb is x-rayed to determine the desired length for the prosthesis. However, in some cases no matter how accurate the x-ray and resulting measurements, certain errors creep in that make accurate measurement of the length of the long bone difficult. For instance, it is often particularly difficult to obtain an accurate x-ray of the upper arm, or humerus bone, of a patient. In a typical scenario, the bone cannot be oriented perfectly parallel with the x-ray plate due to the presence of muscle and fatty tissue around the bone, and other biomechanical disruptions. Thus, often the humerus bone is frequently oriented in a non-parallel relation to the x-ray photographic plate, and most frequently angled slightly outward form the x-ray plate. With this parallax error, it is virtually impossible to accurately determine the length of the humerus bone.

Inaccurate measurement of the long bone prosthesis of course leads to an improper length of the extremity. This maladjusted length can cause motor and muscular difficulties. Moreover, an incorrect prosthesis length can affect the tightness of the tissue surrounding the prosthesis. If the length is too short, the surrounding tissue is unnecessarily loose. If the prosthesis is too long, the tissue may be too tight, if the prosthesis can be implanted at all.

While the prior prosthetic devices have gone a long way toward helping patients with bone or joint disorders, several needs remain unmet. One need is for a viable long bone prosthesis or substitute. Another need is for an adjustable length prosthesis that allows for easy and ready adjustments in situ once the prosthesis has been implanted within the patient.

SUMMARY OF INVENTION

In order to address these needs, the present invention contemplates an adjustable long bone prosthesis that can be readily adjusted within the patient to account for discrepancies in the measurement of a long bone to be replaced. The inventive prosthesis includes a first elongated component having a first end configured to engage a first prosthetic joint, such as an elbow joint, and an opposite end having a first articulating portion. A second elongated component is provided having a second end configured to engage a second prosthetic joint, such as a shoulder joint, and an opposite end having a second articulating portion. The two articulating portions are adjustably mateable with each other so that the combined length of said first and second components can be adjusted to approximate the length of the long bone to be replaced.

In one feature of the invention, the first articulating portion includes an elongated stem, while the second articulating portion includes a collet having a threaded outer surface and an inner surface arranged for pressure engagement of the stem therein. The prosthesis further includes a lock nut having a tapered inner threaded surface configured for threaded engagement with the threaded outer surface of the collet. With this feature, threading the lock nut onto the collet compresses the collet about the elongated stem therein to fix the relative axial and rotational position of the two components.

In accordance with the invention, the second articulating portion also includes a blind bore sized contiguous with the inner surface of the collet. The blind bore is sized for a close running fit with the elongated stem so that the stem can be freely rotated or translated relative to the bore. In certain embodiments, the stem and bore can define an interdigitating interface therebetween. The interdigitating interface can be configured for indexed rotation or translation of the stem relative to the bore. Alternatively, the interdigitating interface can be configured to prevent or limit relative rotation or translation between the components. In a specific embodiment, the interdigitating interface includes a number of axial ribs on the stem and the bore.

The inner surface of the collet and the outer surface of the stem can collectively include a surface treatment configured to enhance the pressure fixation or engagement of the collet about the stem. This surface feature can be in the form of an interdigitating interface between the components or in the form of deformable projections.

It is one object of the invention to provide a prosthesis that is readily adapted as a long bone replacement. A further object resides in features of the invention that allow for easy adjustment of the length of the prosthesis within the patient.

One benefit of the invention is realized in the ability to permit length adjustment and achieve a strong engagement in the adjustable length prosthesis. Another benefit is that the components can be readily adapted for many skeletal structures and replacement of a number of long bones. A further benefit is that the components of the prosthesis can be "mixed and matched" among a selection of components depending on the patient's anatomy.

Other objects and benefits of the invention can be discerned from the following written description and accompanying figures.

DESCRIPTION OF FIGURES

FIG. 1 is a perspective view of an adjustable long bone prosthesis in accordance with one embodiment of the present invention.

FIG. 2 is a top elevational view of the prosthesis shown in FIG. 1.

DESCRIPTION OF PREFERRED EMBODIMENTS

Figure 3:
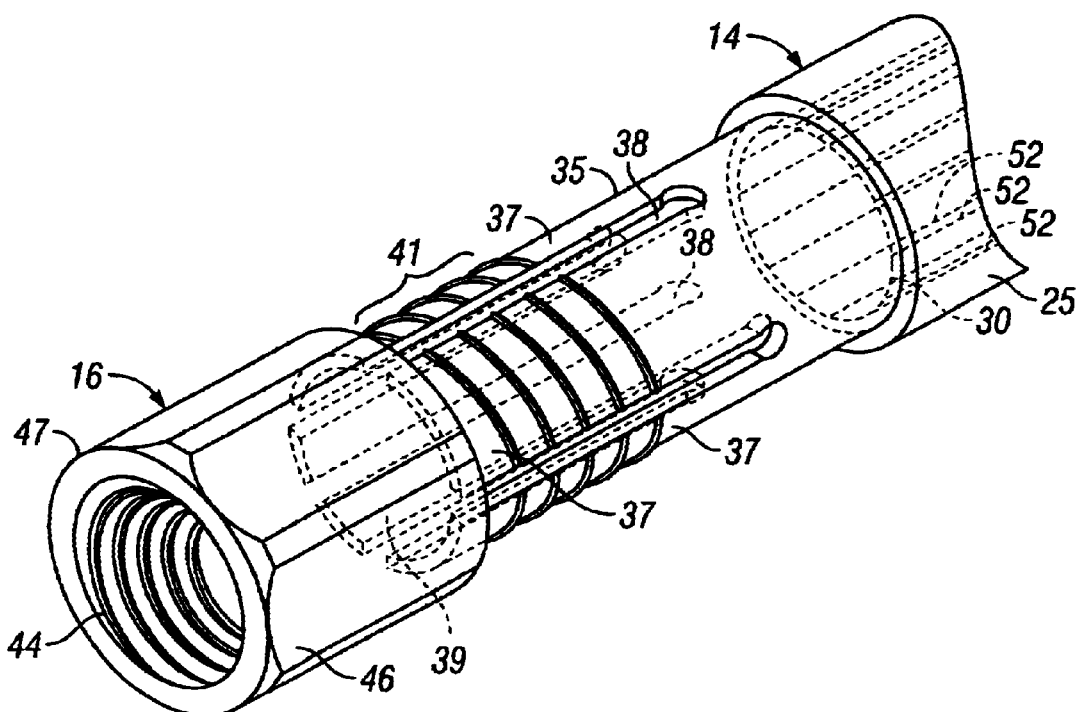
FIG. 3 is an enlarged end perspective view of a collet and locking nut feature of the prosthesis shown in FIGS. 1 and 2.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

The present invention contemplates an adjustable prosthesis that permits adjustment of the length of the prosthesis in situ most preferably, the invention has application for the replacement or substitution of a long bone of a patient, such as the humerus bone. However, the adjustability features of the present invention can be implemented for other prosthesis, such as prosthetic joints. In one aspect of the invention, the adjustable prosthesis utilizes a threaded collet and tapered nut for providing a pressure engagement between articulating components of the prosthesis.

Referring now to FIGS. 1 and 2, an adjustable prosthesis 10 is depicted as including a lower articulating portion 12 that is configured for adjustable articulating engagement with an upper articulating portion 14. In accordance with the illustrated preferred embodiments, the prosthesis 10 is intended as a humeral prosthesis. Thus, the two articulating portions 12 and 14 are intended to approximate the humerus bone of the patient. For the purposes of the following description, the lower articulating portion may be referred to as the elbow humeral component 12 while the upper portion may be referred to as the shoulder humeral component 14. It is of course understood that the upper and lower portions can be modified depending on the nature of the prosthesis. For instance, the prosthesis can be provided for replacement of a different long bone. Likewise, one or both of the portions 12 and 14 can be modified for engagement within an existing bone. For instance, the prosthesis 10 can be implemented as a substitute for middle portion of a long bone.

In the illustrated embodiment, the elbow humeral component 12 includes an elbow joint element 18 formed at the free end of the component. Similarly, the shoulder humeral component 14 includes a shoulder joint element 20 formed at its free end. In a specific embodiment, the elbow joint element 18 can form part of the modular elbow disclosed in U.S. Pat. No. 6,290,725. The pertinent portion of this disclosure is incorporated herein by reference, most particularly the portion describing the humeral components of the modular elbow. Likewise, the shoulder joint element 20 can be configured as shown is U.S. Pat. No. 5,314,479. The pertinent disclosure of the '479 is incorporated herein by reference, most specifically the portion of the disclosure discussing the prosthesis bodies configured to engage the joint head members.

As shown in FIG. 1, the elbow humeral component 12 includes a lower elongated member 25, while the shoulder humeral component 14 includes an upper elongated member 27. The upper member defines a blind bore 30 extending into one end thereof (i.e., the end opposite the shoulder joint element 20). The lower elongated member 25 defines an elongated stem 32 that is sized for a close running fit within the bore 30. The stem 32 is defined at the end of the member 25 opposite the elbow joint element 18.

In accordance with one important aspect of the invention, the upper elongated member 25 further defines a collet portion 35 integrated into the end of the elongated member 27 at the blind bore 30. As shown in FIG. 3, the collet portion 35 is defined by a number of collet fingers 37 separated by slots 38. The fingers 37 define a bore 39 that is substantially contiguous with the blind bore 30 in the upper elongated member 27. Preferably, the bore 39 and the blind bore 30 are each formed at the same diameter and most preferably in a common drilling and reaming operation.

As shown in FIGS. 1 and 2, a lock nut 16 is disposed over the collet portion 35. More specifically, the collet portion 35 defines a series of outer threads 41 along its exterior surface and extending over a substantial portion of the length of the collet portion 35. The lock nut 16 includes mating inner threads 44 that are configured for threaded engagement with the outer threads 41 of the collet portion.

In accordance with the present invention, the combination of the lock nut 16, collet portion 35 and stem 32 of the lower elongated member 25, provides for a pressure engagement or lock between the lower and upper articulating components 12 and 14. More specifically, the inner surface 58 (FIG. 5) of the collet portion 35 is compressed against the outer surface of the stem 32 by threaded engagement of the lock nut 16 onto the outer threads 41 of the collet portion 41. To achieve this pressure lock function, it is necessary that the collet portion 35 be radially compressible to attempt to reduce the diameter of the bore 39 to a dimension less than the outer diameter of the stem 32. In the preferred embodiment, this reduction is accomplished by making the lock nut 16 a tapered nut. More specifically, the inner bore 35 of the nut 16 is tapered from a larger diameter at the end facing the collet portion 35, to a smaller diameter at the end facing the elbow humeral component 12. Most preferably, the smaller diameter portion of the tapered bore 45 within lock nut 16 is small enough to produce an interference fit between the collet portion 35 and the stem 32. In this way, the amount of pressure fixation force can depend upon the degree which the lock nut 16 is threaded over the collet portion 35.

In accordance with the preferred embodiment, it is anticipated that the collet portion 35 includes outer threads that extend along the length of the collet portion a sufficient distance to accept the length of the inner threads of the lock nut 16. With this approach, the collet portion can be completely hidden behind the lock nut 16 to reduce the likelihood of soft tissue injury once the prostheses has been implanted within the patient.

In the most preferred embodiment, the inner bore 45 of the nut is tapered. In alternative embodiments, the outer threaded surface 41 of the collet portion 35 can be tapered with the inner threads 44 of the lock nut 16 having a constant diameter. Similarly, the inner bore 39 of the collet portion can be tapered with the outer diameter of the collet portion and the inner diameter of the lock nut remaining constant. In any of these configurations, threading the lock nut 16 onto the collet portion 35 exerts a radially inward compressive pressure or force against the stem 32, thereby locking the two articulated components 12 and 14 together. In a specific embodiment, the angle implemented can be a Morse angel of about 1–3°. Both the lock nut 16 and the collet portion 35 can utilize the same Morse angle to enhance the fixation between the lock nut and the collet portion.

In accordance with a preferred embodiment of the invention, the stem 32 is sized for a close running fit in both rotation and translation relative to the blind bore 30 and collet bore 39. In other words, in the preferred embodiments the elbow humeral component 12 can articulate relative to the shoulder humeral 14 in both angular and extensional directions. In this way, the length of the prosthesis 10 can be adjusted to approximate the length of the patient's original bone, and the angular orientation between the joint elements 18 and 20 can be adjusted by rotating the stem 32 relative to the blind bore 30. In a specific embodiment, the close running fit between the stem and bore can be about 0.10 inches (2.5 mm) radially.

Figure 4:
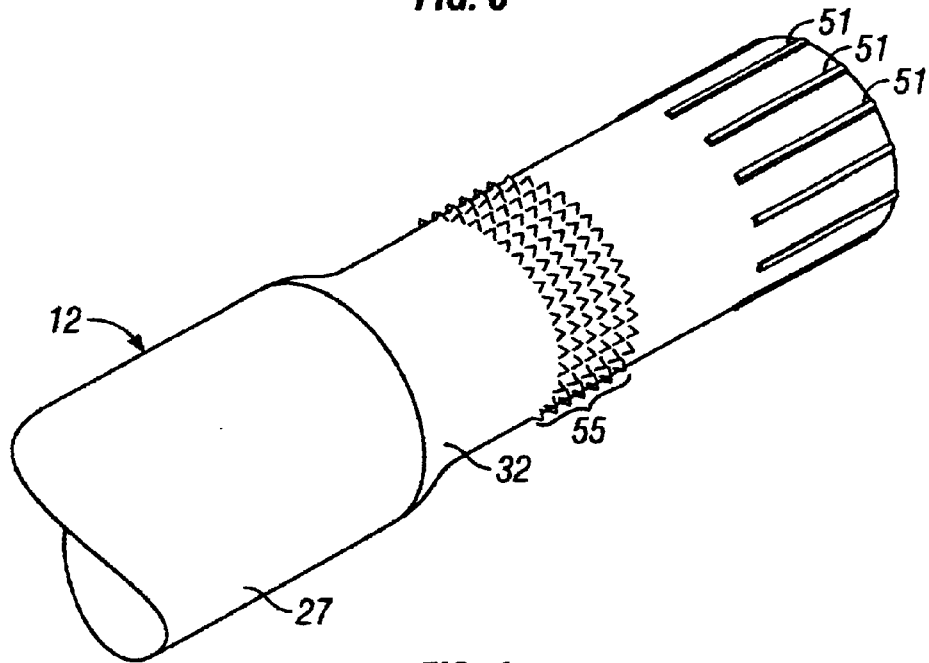
FIG. 4 is an enlarged perspective view of an end portion of a lower articulating portion of the prosthesis shown in FIGS. 1 and 2.
Figure 5:
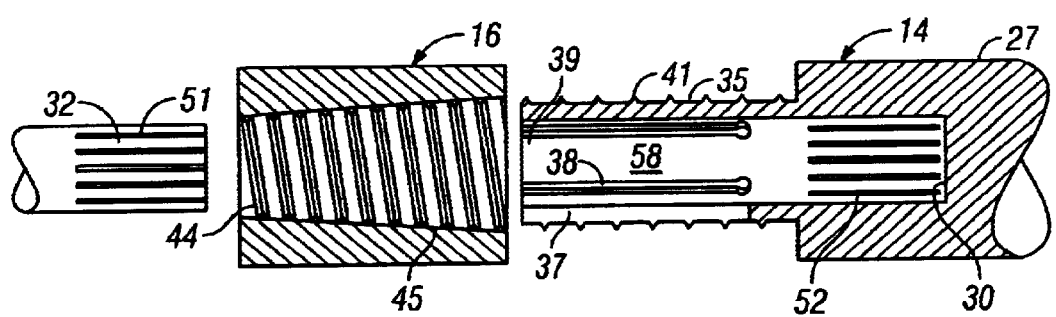
FIG. 5 is a side cross-sectional view of the articulating components and lock nut prior to engagement with each other.

In order to assist in setting the angular orientation between the two components 12 and 14, interdigitating of ribs 51 on the stem 32 and ribs 52 on the blind bore 30 can be implemented (FIGS. 3–5). Preferably, with this embodiment, the ribs 51 and 52 only barely project above their corresponding surfaces. In this way, the interdigitating ribs 51 and 52 do not impede relative rotation between the elbow humeral component 12 and the shoulder humeral component 14. Instead, the ribs 51, 52 can offer a slight resistance at periodic intervals of angular movement, and can even generate a clicking sound indicative of a particular indexed angle of rotation. For example, the interdigitating nibs 51 can be disposed at 10° intervals around the diameter of the stem 32. A single rib can be implemented on one of the two components, particularly where only an audible indication is necessary. Alternatively, a greater number of ribs can be implemented on one element relative to the other. Preferably, the ribs 51, 52 can have a height slightly greater than half the running radial fit, such as 0.06 inches (1.5 mm) in a specific embodiment In certain instances, relative rotation between the two components 12 and 14 is undesirable, and even detrimental. In embodiments of the prosthesis of this type, the interdigitating ribs 51 and 52 can be more prominent with respect to the corresponding elements 32, 30. In other words, the ribs 51 and 52 can be configured so that no rotation between the two components is possible. In some embodiments, an interlocking spline configuration can be implemented for the ribs 51 and 52. With this configuration, the blind bore 30 can be provided with either elongated channels or upstanding splines, while the stem 32 can be complimentary configured with upstanding splines or channels. Thus, once the stem 32 is extended into the blind bore 30, the angular position between the components 12 and 14 is fixed, regardless of the position of the lock nut 16 on the collet portion 35. In alternative embodiments, the shapes of the bore and stem can be non-circular complementary shapes, such as oval or square, to prevent relative rotation.

In a similar fashion, circumferential ribs can be provided on the articulating components to provide for indexed length adjustment. Thus, the ribs 51 on the stem 32 can extend around the circumference of the stem at predetermined axial intervals. The rib 52 in the blind bore 30 can be modified to be a single rib or projection at the mouth of the bore that provides minimal resistance to penetration of the stem 32 into the bore 30. Again, the modified ribs can provide an audible click to indicate indexed length positions of the humeral components 12, 14.

As a further option, the stem and bore can be provided with a retention feature that helps hold the components together prior to implantation in the patient. This retention feature can include a circumferential rib at the end of the stem and a corresponding circumferential rib at the end of the bore, where the two ribs provide an interference fit. The interference is overcome when the stem is initially pushed into the bore, and is sufficient to hold the stem in place when subject to normal manipulation.

The stem 32 can include a surface feature 55 configured to enhance the pressure fixation and grip of the collet portion 35 on the stem 32. A similar surface feature can be implemented on the inner surface 58 of the collet portion 35. A variety of surface treatments are contemplated, provided that the treatments enhance or increase the pressure fixation between the components when the lock nut 16 is fully threaded onto the collet portion 35. For instance, the surface feature 55 can include a knurling pattern, circumferential and/or longitudinal splines, or deformable protrusions. A similar treatment can be provided to inner surface 58 of the collet portion 35.

As should be appreciated from the foregoing description, and upon viewing FIGS. 1 and 2, as well as the exploded view in FIG. 5, the adjustable prosthesis 10 can be easily adjusted when the prosthesis is situated in the patient. In order to effect adjustments, it is only necessary to leave the locking nut 16 un-tightened relative to the collet portion 35. The overall length of the prosthesis 10 can be adjusted by changing the amount that the stem 32 extends into the blind bore 30. Thus, the overall combined length of the humeral components 12 and 14 can be specifically calibrated within the patient to ensure a prosthesis length that is anatomically correct for the particular patient. In addition, the angular positioning between the two joint elements 18 and 20 can be adjusted.

Once the components have been situated at their prescribed positions, the lock nut 16 can be threaded onto the collet portions 35. Preferably, the lock nut 16 is configured to engage a wrench, by including an outer wrench surface 46. In one preferred feature of the invention, the outer wrench surface 46 includes only rounded edges 47, to reduce the risk of trauma to the surrounding soft tissue. As shown in FIG. 3, the wrench surface 46 can be configured to accommodate a hex wrench. Of course, other wrench surface configurations can be provided to engage a variety of wrenches.

It is preferable that the coarseness of the engaging of threads 41 and 49 be calibrated so that excessive rotation of the lock nut 16 is not required to accomplish a solid fixation. On the other hand, a certain fineness to the threads is also desirable to enhance the fixation between the components and reduce the likelihood that the lock nut 16 will become unthreaded from the collet portion 35. As further insurance against this undesirable event, a biocompatible adhesive can be utilized between the lock nut 16 and collet 35. In addition, the Morse taper feature can be incorporated between the locking and/or articulating components. As a further alternative, the lock nut 16 can be supplemented by an additional lock nut that can be threaded against the lock nut 16 to prevent its counter-rotation.

A further feature of the present invention can be appreciated upon review of FIGS. 2 and 5. In particular, the shoulder humeral portion 14, and specifically its upper elongated member 27, exhibits a particular outer diameter. Preferably, the outer diameter approximates the diameter of the long bone being replaced. In addition, this upper elongated member 27 accounts for the majority of the overall length of the prosthesis 10. In order to maintain the overall continuity of the prosthesis, the lock nut 16 can have an outer dimension that is not substantially greater than the diameter of the elongated member 27, and is actually preferably smaller in diameter than that portion. Likewise, the lower elongated member 25 of the elbow humeral component 12 can have an outer diameter that is less than or equal to the outer diameter of the upper elongated member 27. In this way, the overall profile of the prosthesis 10 is smooth and presents as little disruption to the surrounding tissue of the patient than is necessary.

Most preferably, the components 12 and 14 and lock nut 16 are formed as a biocompatible metallic material, such as titanium. It is also preferable that the material be x-ray opaque so that the continued viability of the prosthesis can be judged at subsequent x-rays. In a specific embodiment in which the prosthesis 10 is intended for replacement of the humerus, the shoulder humeral component 14 can have an outer diameter of about 0.75 inches (20 mm) and a length from the base of the shoulder joint element 20 to the base of the collet portion 35 of about 4.25 inches (110 mm). The collet portion 35 can extend about 1.0 inches (25 mm) from the end of the upper elongated member 27, and have an outer diameter of about 0.5 inches (13 mm) and a bore diameter of about 0.4 inches (10 mm).

The elbow humeral component 12, and particularly the lower member 25, can have a length from the elbow joint element 18 to the base of the stem 32 of about 2.1 inches (53 mm) with a diameter of 0.55 inches (14 mm). The stem 32 has a diameter slightly less than the diameter of the bore 39, and a length from the end of the lower elongated member 25 of about 1.5 inches (38 mm). The lock nut 16 can have a length of about 0.95 inches (24 mm).

It should be appreciated that while the important feature of the present invention allows in situ adjustments to the prosthesis when it is intentionally implanted, this same feature permits subsequent adjustments of the length and/our orientation of the prosthesis. Thus, if a certain amount of slippage occurs over time or due to a traumatic load, the lock nut 16 can be loosened, thereby allowing readjustment of the upper and lower compotes 25 and 27. It should also be appreciated that the modular aspect of the prosthesis 10 allows a lot of the other components 12 and 14 to be replace. For instance, if a new elbow joint is developed which requires a different elbow joint element, the elbow humeral component 12 can be replaced with the newly designed component. This same capability is beneficial during the initial surgery, since it allows mixing and matching of various shoulder and elbow components as dictated by the patient's anatomy.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

For instance, the present invention contemplates configuring both of the elongated members 25 and 27 to be engaged within the intramedullary canal of a sustained bone of a patient. Thus, one end of the prosthesis can be engaged to a bone segment, while the other end is engaged to a joint element. Similarly, both ends can be engaged to a bone segment, with the prosthesis providing a replacement for a middle portion of an existing bone. As indicated above, the illustrated embodiment concerns a replacement for the humerus, while the principles of the invention can be applied to other bones, especially human long bones such as the femur, tibia, fibula, ulna, and radius.

In addition, the blind bore 30 and stem 32 are described above as integrated into the upper member 27 and lower member 25, respectively. It should be apparent that the bore and stem can be switched to the opposite member and still retain the functionality of the present invention.

What is claimed is:

1. An adjustable long bone prosthesis comprising:
   a first elongated component having a free end and an opposite end having an elongated stem;
   a second elongated component having a free end and an opposite end having an articulating portion adjustably mateable with said elongated stem so that said first and second components define an adjustable length to approximate the length of a long bone, said articulating portion including a collet having a threaded outer surface and an inner surface arranged for pressure engagement with said elongated stem when said collet is compressed about said stem; and
   a nut having a threaded inner surface in threaded engagement with said outer surface of said collet, wherein at least one of said collet and said nut defines a tapered surface arranged so that threading said nut onto said collet compresses said collet about said elongated stem.

2. The adjustable long bone prosthesis according to claim 1, wherein said threaded inner surface of said nut includes said tapered surface.

3. The adjustable long bone prosthesis according to claim 1, wherein said tapered surface is tapered at a Morse angle.

4. The adjustable long bone prosthesis according to claim 1, wherein:
one of said first component or said second component defines a maximum outer diameter at said opposite end thereof; and
said nut defines an outer dimension approximating or less than said maximum outer diameter.

5. The adjustable long bone prosthesis according to claim 1, wherein said first component includes an elongated body between said free end and said stem, said body defining an outer dimension that is greater than an outer dimension of said stem.

6. The adjustable long bone prosthesis according to claim 1, wherein said free end of at least one of said first and second components is configured to mate with a prosthetic joint.

7. The adjustable long bone prosthesis according to claim 6, wherein said free end of both of said first and second components is configured to mate with a corresponding prosthetic joint.

8. The adjustable long bone prosthesis according to claim 7, wherein said free end of one of said first and second components is configured to mate with a prosthetic elbow joint and said free end of the other of said first and second components is configured to mate with a prosthetic shoulder joint.

9. The adjustable long bone prosthesis according to claim 1, wherein at least one of said elongated stem and said inner surface of said collet define a surface feature configured to enhance the pressure engagement therebetween.

10. The adjustable long bone prosthesis according to claim 9, wherein said elongated stem and said inner surface of said collet define an interdigitating interface therebetween.

11. The adjustable long bone prosthesis according to claim 1, wherein said nut has an outer surface configured for engagement with a wrench.

12. The adjustable long bone prosthesis according to claim 11, wherein said outer surface includes only rounded edges.

13. The adjustable long bone prosthesis according to claim 1, wherein said articulating portion includes a bore sized for a close running fit with said elongated stem.

14. The adjustable long bone prosthesis according to claim 13, wherein at least one of said elongated stem and said bore define a surface feature configured for indexed axial movement of said stem relative to said bore.

15. The adjustable long bone prosthesis according to claim 13, wherein said elongated stem and said bore are cooperatively configured to prevent relative rotation between said stem and said bore.

16. The adjustable long bone prosthesis according to claim 13, wherein said elongated stem and said bore define an interdigitating interface therebetween.

17. The adjustable long bone prosthesis according to claim 16, wherein said interdigitating interface is configured for indexed rotation of said stem relative to said bore.

18. The adjustable long bone prosthesis according to claim 16, wherein said interdigitating interface includes a number of axial ribs on said stem and said bore.

19. An adjustable prosthesis for replacement of at least a portion of a bone comprising:

a first component having an elongated stem;

a second component having an articulating portion adjustably mateable with said elongated stem so that said first and second components define an adjustable length to approximate the length of the portion of the bone being replaced, said articulating portion including a collet having a threaded outer surface and an inner surface arranged for pressure engagement with said elongated stem when said collet is compressed about said stem; and a nut having a threaded inner surface in threaded engagement with said outer surface of said collet, wherein at least one of said collet and said nut defines a tapered surface arranged so that threading said nut onto said collet compresses said collet about said elongated stem.

20. The adjustable long bone prosthesis according to claim 19, wherein said threaded inner surface of said nut includes said tapered surface.

21. The adjustable long bone prosthesis according to claim 19, wherein:
one of said first component or said second component defines a maximum outer diameter at said opposite end thereof; and
said nut defines an outer dimension approximating or less than said maximum outer diameter.

22. The adjustable long bone prosthesis according to claim 19, wherein said first component includes an elongated body between said free end and said stem, said body defining an outer dimension that is greater than an outer dimension of said stem.

23. The adjustable long bone prosthesis according to claim 19, wherein said articulating portion includes a bore sized for a close running fit with said elongated stem.

24. The adjustable long bone prosthesis according to claim 23, wherein said elongated stem and said bore define an interdigitating interface therebetween.

25. An adjustable long bone prosthesis comprising:

a first elongated component having a first end configured to engage a first prosthetic joint and an opposite end having a first articulating portion;

a second elongated component having a second end configured to engage a second prosthetic joint and an opposite end having a second articulating portion adjustably mateable with said first articulating portion so that the combined length of said first and second components is adjustable to approximate the length of a long bone.

26. The adjustable long bone prosthesis according to claim 25, wherein:
said first articulating portion includes an elongated stem; and
said second articulating portion includes;
a collet having a threaded outer surface and an inner surface arranged for pressure engagement of said stem therein; and
a lock nut having a tapered inner threaded surface configured for threaded engagement with said threaded outer surface, whereby threading said lock nut onto said collet compresses said collet about said elongated stem therein.

* * * * *